(12) United States Patent
Hiramoto et al.

(10) Patent No.: US 6,294,161 B1
(45) Date of Patent: *Sep. 25, 2001

(54) DEODORANT COMPOSITION

(75) Inventors: Tadahiro Hiramoto; Kenji Saiki; Tetsuharu Okazaki, all of Kanagawa (JP)

(73) Assignee: Takasago International Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/016,281

(22) Filed: Jan. 30, 1998

(30) Foreign Application Priority Data

Jan. 30, 1997 (JP) .................................................. 9-029814

(51) Int. Cl.$^7$ ................. A61L 9/00; A61L 9/01; A61K 9/68; A61K 35/78
(52) U.S. Cl. ................ 424/76.1; 48/76.2; 48/76.21; 48/195.1; 48/440
(58) Field of Search ................................ 424/76.1, 76.2, 424/48, 440, 76.21

(56) References Cited

U.S. PATENT DOCUMENTS

| | | | | |
|---|---|---|---|---|
| 5,431,912 | * | 7/1995 | N'Guyen | 424/401 |
| 5,747,053 | * | 5/1998 | Nashimoto et al. | 424/405 |
| 5,804,170 | * | 9/1998 | Negishi et al. | 424/65 |

OTHER PUBLICATIONS

"Effect of Polyphenol Oxidase on Deodorization," Osamu Negishi and Tetsuo Ozawa, Biosci, Biotech, Biochem, 61 (12), 2080–2084 (1997).

* cited by examiner

*Primary Examiner*—Shelley A. Dodson
(74) *Attorney, Agent, or Firm*—Sughrue, Mion, Zinn, Macpeak & Seas, PLLC

(57) ABSTRACT

A deodorant composition having an excellent effect of deodorizing bad breath, refrigerator odors, and odors from pets and domestic animals, and which does not adversely affect the environment. The composition contains (i) at least one natural extract selected from the group consisting of Rosemary extract, sunflower seed extract, raw coffee bean extract, tea extract, grape pericarp extract, grape seed extract and apple extract, and (ii) an enzyme capable of oxidizing phenolic compounds.

16 Claims, No Drawings

DEODORANT COMPOSITION

FIELD OF THE INVENTION

The present invention relates to a deodorant composition and more particularly to a deodorant composition used for eliminating odors from the environment that are offensive to humans, such as bad breath, refrigerator odors, pet and domestic animal odors, factory odors or offensive odors in industrial effluent.

BACKGROUND OF THE INVENTION

There are various odors around us, such as refrigerator odors, bad breath and odors from domestic animals. Because some of these odors are unpleasant to humans, a wide variety of approaches have been proposed to eliminate these odors. One such conventional deodorizing method is a method of adsorbing and eliminating the substance causing the offensive odor. Examples of deodorant substances used in such a method are activated carbon and catechin-containing tea.

However, activated carbon is disadvantageous in that it cannot sufficiently remove trace amounts of a substance, it cannot be added to foods for human consumption, and its use can cause environmental problems when activated carbon having a large amount of substance adsorbed thereon is discharged. In this regard, naturally occurring substances such as catechin are harmless toward the environment and can be blended with chewing gum and the like to eliminate bad breath. However, catechins do not provide a sufficient deodorant effect.

SUMMARY OF THE INVENTION

In view of the above, it is therefore an object of the present invention to develop a deodorant composition having excellent deodorant effects on bad breath, refrigerator odors, and odors from pets and domestic animals, and which deodorant composition does not harm the environment.

Japanese Patent Application No.212,999/95 previously filed by the present inventor describes that phenolic compounds such as catechins have deodorant properties, and that the effect is surprisingly improved by allowing polyphenol oxidase to coexist with these compounds. However, the materials proposed in this prior application were chemically synthesized substances. On the other hand, more recently, people have become concerned about the adverse effects of chemically synthesized substances on humans such that consumers refrain from using such products. Accordingly, the present invention has been achieved by employing naturally occurring substances, particularly natural extracts containing phenolic compounds for use as food additives or as foods.

That is, the present invention relates to a deodorant composition comprising (i) one or more natural extracts selected from the group consisting of rosemary extract, sunflower seed extract, raw coffee bean extract, tea extract, grape pericarp extract, grape seed extract and apple extract, and (ii) an enzyme which is capable of oxidizing phenolic compounds.

It is considered that the mechanism of the deodorant action of phenolic compounds in natural extracts is that these compounds are oxidized by oxygen in the atmosphere to form a highly reactive quinone structure. The quinone further reacts with a substance having an offensive odor to eliminate the same. Furthermore, in the present invention, an enzyme capable of oxidizing phenolic compounds is provided in the presence of the natural extract containing phenolic compounds to promote this auto-oxidation reaction, thus rapidly eliminating offensive odors at a high deodorization rate.

DESCRIPTION OF THE PREFERRED EMBODIMENTS

The present invention is described in detail below.

The natural extract, namely, one of the two components in the deodorant composition of the present invention, comprises one or more extracts selected from rosemary extract, sunflower seed extract, raw coffee bean extract, tea extract, grape pericarp extract, grape seed extract and apple extract. The extract of the present invention is not particularly limited as long as it contains a phenolic compound that has been extracted with water, alcohol, an organic solvent or a mixture thereof. The extraction solvent is selected depending on the desired use of the deodorant composition.

When the composition is to be used as a deodorant agent for food, the solvent used therefor must also be selected from solvents acceptable for addition to foods. Examples of such solvents include water, ethanol, propanol, butanol, acetone, hexane, propylene glycol, water-containing ethanol, water-containing propylene glycol, etc., preferably hot water, water-containing ethanol and water-containing propylene glycol.

The natural source for the extract includes rosemary, sunflower seeds, raw coffee beans, tea, grape pericarp, grape seeds and apples, and two or more of these may be used in combination. The extraction conditions may be usual extraction conditions. Also, the resulting extract is concentrated under reduced pressure and stored as a concentrate, and may be diluted before use at a suitable concentration for preparing the deodorant composition.

The enzyme capable of oxidizing phenolic compounds, that is, the second component in the deodorant composition of the present invention, is an enzyme having the activity of oxidizing said phenolic compound into a compound with a quinone structure or an enzyme having the action of adding a phenolic hydroxy group for oxidation into quinone.

Any enzyme having this action can be used and examples thereof include polyphenol oxidase, monophenol oxidase, oxidase forming hydrogen peroxide and peroxidase. More specifically, preferable enzymes include laccase, tyrosinase, glucose oxidase and peroxidase, and a burdock enzyme, pear enzyme, etc., obtained from natural sources can also be used. Two or more of these enzymes can be used in combination.

A material or composition containing said enzyme is also within the scope of the present enzyme capable of oxidizing phenolic compounds. Examples include an extract from a plant containing said enzyme, an extract from fungi containing said enzyme, and powder containing such an extract, for example, acetone powder (an acetone-dried preparation as prepared in Reference Example 1 below).

Plants containing said enzyme preferably include fruits and vegetables such as apple, pear, burdock etc., and fungi containing said enzyme include mushrooms of the genera Agaricus and Boletus such as Agaricus bisporus and Boletus pulverulentus.

These enzymes are not limited to commercially available enzymes, but may also be prepared according to conventional methods.

The deodorant composition of the present invention may further comprise conventional ingredients such as carriers, stabilizers and fillers added to and mixed with said two components.

The deodorant composition of the present invention can eliminate offensive odors. Examples of substances having such offensive odors include sulfur-containing compounds such as mercaptan or nitrogen-containing compounds such as indole, skatole, ammonia, urea, amines, etc.

Deodorization by the deodorant composition of the present invention is achieved by catalytic reaction with said composition in the presence of offensive odors. More particularly, the deodorant compositions and substances which release offensive odors are preferably mixed to permit the reaction to proceed easily, especially where water may be advantageously present to permit the reaction to proceed more smoothly.

Although the temperature in this reaction varies depending on the type of enzyme and may be any temperature at which the enzyme reaction proceeds, the reaction proceeds more rapidly when the enzyme is mixed in the range of room temperature to 40° C. Furthermore, the required reaction time depends on the type and amount of enzyme used, but a period of time ranging from a few minutes to several dozens of hours will usually suffice. Other conditions are not particularly limited if they are adapted to the circumstances under which the enzyme reaction may proceed.

The deodorant composition of the present invention comprises a natural extract containing a polyphenol compound, i.e., a deodorant base material, and an enzyme for oxidizing the same. Thus, the polyphenol compound is used in an activated form, to permit the reaction to proceed rapidly and to provide superior effects. When the present deodorant composition is used for the elimination of bad breath, an enzyme derived from foods such as vegetables or mushrooms is used to render the deodorizing method extremely safe. When offensive odors in the environment are to be eliminated, there is no problem with environmental pollution.

The addition amount of the natural extract is determined depending on the polyphenol content. In general, a natural extract containing from 2 to 100 mg of polyphenol compounds is added per about 100 mg of the deodorant composition. The addition amount of the enzyme capable of oxidizing phenolic compounds and a natural source containing the enzyme is determined depending on its enzyme activity, from 50 to 1000 units as defined in Reference Example 1 below, and may be any amount which allows the enzyme to oxidize phenolic compounds. The enzyme or a natural source containing the enzyme is preferably added in an amount which provides more than 100 units of enzyme activity per about 100 mg of the deodorant composition to permit the reaction to proceed more rapidly.

EXAMPLES

Hereinafter, the present invention is described in more detail with reference to the following Examples. However, the present invention should not be construed as being limited thereto.

Reference Example 1
Preparation of Enzyme Capable of Oxidizing Phenolic Compounds 400 ml of acetone at −20° C. was introduced into 100 g of a plant or mushroom, and the sample was disrupted with a mixer and then filtered under suction. The residue was washed sufficiently with 500 ml of 80% aqueous acetone. The residue was lyophilized into a powder. The yield was 20% in the case of burdock.

Measurement of Specific Activity of the Plant-Derived Enzyme Extract

The sample was allowed to react with L-dopa (Nakarai Tesque K.K.) as a substrate in 3 ml of phosphate buffer, pH 6.5, where 1 unit was defined as the amount of enzyme causing an increase of 0.001 in absorbance at 265 nm in the UV region at 25° C. for 1 minute.

Burdock extract (10 mg)=644 units.
Pear extract (10 mg)=130 units.
Apple extract (10 mg)=530 units.
Commercial mushroom-derived polyphenol oxidase (PPO) (Sigma Chemical Co.) was also used as a commercial product of the enzyme.

Reference Example 2
Preparation of Extracts from Natural Sources
(1) Rosemary Extract (a Product of Tokyo Tanabe Co., Ltd.)

1 liter of ethanol with a water content of 40 to 60% was added to 100 g of rosemary leaves and flowers and refluxed for 3 hours under heating. The mixture was then filtered when warm to provide a filtrate containing anti-oxidant components (referred to hereinafter as "treatment extraction"). The residue was further extracted two more times, and the resulting filtrates were combined with the above filtrate. By adding 500 ml of water to the combined extract, water-insoluble antioxidant components were precipitated, and 10 g of activated carbon was further added thereto followed by stirring. This solution was stored overnight in a cool place and filtered to provide a filtrate. This filtrate was concentrated under reduced pressure to provide a fraction (solid) of water-soluble phenolic components (Japanese Patent Appln. Laid-Open Publication No. 18435/80).

(2) Sunflower Seed Extract (a Product of Dainippon Ink and Chemicals, Inc.)

Ethanol containing 60% (v/v) water was added to mechanically ground seeds of sunflower, and the seeds were extracted at 60° C. for 7 hours. After centrifugation under cooling, the supernatant was concentrated under reduced pressure and dried to provide a sunflower seed extract (Japanese Patent Appln. Laid-Open Publication No. 132,073/95).

(3) Raw Coffee Bean Extract

Raw coffee beans were ground by a grinder (5 mm in mesh size) and then extracted with water at 85 to 95° C. for 2 hours. The extract was filtered and the filtrate was adsorbed onto an XAD-2 column (Organo K.K.). It was washed with water and eluted with methanol, and the eluate was concentrated and evaporated to dryness to provide a raw coffee bean extract.

(4) Tea Extract (a Product of Mitsui Norin K.K.)

1 kg of green tea was extracted with 10 liters of hot water at 90° C. and the leaves were removed by filtration to provide 8.3 liters of extract. The extract was concentrated into 1 liter to which 1 liter of acetone was then added, and the resulting insolubles were removed by centrifugation. 1 liter of ethyl acetate was added to the supernatant, and the mixture was stirred and left to stand for 30 minutes. The resulting ethyl acetate layer was concentrated under reduced pressure to convert the same into an aqueous layer and then lyophilized to provide 97 g of tea phenol having a purity of 60% (Japanese Patent Appln. Laid-Open Publication No. 20589/92).

(5) Grape Pericarp Extract

Ethanol was added to grape pericarp (variety: Campbell) and extracted at 70° C. for 2 hours under stirring. The extract was concentrated and evaporated to dryness to provide a grape pericarp extract.

(6) Grape Seed Extract (a Product of KIKKOMAN CORPORATION)

Grape seeds were extracted with water at a temperature of 70° C. or more for 10 minutes to 4 hours (Japanese Patent Appln. Laid-Open Publication No. 200781/91).

(7) Apple Extract (a Product of THE NIKKA WHISKEY DISTILLING CO., LTD.)

An apple was disrupted, then squeezed, treated with pectinase for clarification, centrifuged and filtered to provide fruit juice which was then purified through a column (Japanese Patent Appln. Laid-Open Publication No. 259453/96).

(8) Production of Caffeine Depleted Tea 10 g of green tea extract (containing 8.7% by weight of caffeine and 23.0% by weight of polyphenol) was dissolved in 200 ml of water and extracted twice with 200 ml of ethyl acetate. The resulting ethyl acetate extract was concentrated under reduced pressure to about 50 ml, and caffeine was precipitated from the concentrate in a refrigerator at 4° C. and separated by filtration to provide 200 mg of crystals. The filtrate was combined with the aqueous phase used for extraction, then concentrated and evaporated to dryness under reduced pressure to provide 9.8 g of a caffeine depleted fraction (containing 6.7% by weight of caffeine and 23.0% by weight of polyphenol).

The caffeine content and polyphenol content were determined in the following manner.

Method of Measuring Caffeine Content

The caffeine content was determined on the basis of the ratio of its peak to a peak of a purified product in a calibration curve using high performance liquid chromatography.

Column: 5C-18MS (Nakarai Tesque K.K.).
Developing solvent: 0.5% THF/acetonitrile.
Detection: UV 273 nm.
Flow rate: 1 ml/min.

Method of Measuring Polyphenol Content

The Folin-ciocalteu method was used (see Am. J. Enol. Vitic., 16, 144 (1965)).

Examples 1 to 8

50 mg of the above pear enzyme preparation as described in Reference Example 1, 1 ml of water, and 2 µl of about a 15 wt % aqueous methyl mercaptan sodium solution as a substance having an offensive odor were introduced into a 100 ml vial, and 0.5 ml of an aqueous solution of each of the natural extracts (containing 2 mg of phenolic compounds) shown in Table 1 and prepared in Reference Example 2 was added to each vial and shaken by hand. The color of the reaction solution was changed by shaking or allowing it to stand for 10 minutes. 50 ml of gas from each vial was passed through a detector tube (Gastech K.K.), and the concentration of the substance with the offensive odor remaining in the gas was determined. The concentration of the substance with the offensive odor was determined using a gas-detecting tube for detecting $CH_3SH$ (No. 71H, Gastech K.K.). Namely, 50 ml of gas from each vial was passed through the gas-detecting tube for detecting $CH_3SH$, and the concentration of the offensive odor remaining in the gas was determined by the color changed tube length of the gas-detecting tube. The results are shown in Table 1. The control in the following Tables is an example where a natural extract was not used.

TABLE 1

| | Plant Extract | Amount of Offensive Odor Introduced (ml) | Measured Value (ppm) | Degree of Deodorization (%) |
|---|---|---|---|---|
| | Control | 50 | 350 | 0 |
| Example 1 | Rosemary (36.4 mg) | 50 | 0 | 100 |
| Example 2 | Raw coffee beans (7.2 mg) | 50 | 0 | 100 |
| Example 3 | Sunflower seeds (38.5 mg) | 50 | 0 | 100 |
| Example 4 | Tea (2.9 mg) | 50 | 95 | 73 |
| Example 5 | Caffeine depleted tea (2.9 mg) | 50 | 75 | 78 |
| Example 6 | Grape seeds (7.7 mg) | 50 | 135 | 62 |
| Example 7 | Grape pericarp (10.1 mg) | 50 | 200 | 42 |
| Example 8 | Apple (2.7 mg) | 50 | 0 | 100 |

Example 9

The polyphenol content as shown in Table 2 was adjusted with the addition of rosemary extract (containing 5.5% by weight of polyphenol). For example, 36.4 mg of the rosemary extract was added to obtain a polyphenol content of 2 mg, and 72.8 mg of the rosemary extract was added to obtain a polyphenol content of 4 mg. Each of the samples and 10 mg of the burdock enzyme were used to determine the degree of deodorization in the manner according to Example 1. The results are shown in Table 2.

TABLE 2

| Plant Extract | Polyphenol Content (mg) | Amount of Offensive Odor Introduced (ml) | Measured Value (ppm) | Degree of Deodorization (%) |
|---|---|---|---|---|
| Control | 0 | 50 | 300 | 0 |
| Rosemary | 2 | 50 | 165 | 45 |
| Rosemary | 4 | 50 | 100 | 66.7 |
| Rosemary | 6 | 50 | 75 | 75 |
| Rosemary | 8 | 50 | 0 | 100 |

Examples 10 to 16

1.5 ml of 0.05 M phosphate buffer (pH 7.0) was added to a 100 ml vial containing a predetermined amount of each of the natural extracts (containing 2 mg of a phenolic compound) as shown in Table 3. Then, 10 mg of the burdock enzyme, 50 mg of the pear enzyme and 1 mg of PPO as enzyme preparations were added respectively to each vial as shown in Table 3. 2 µl of about a 15% aqueous $CH_3SNa$ solution was further added to each vial which was then sealed with a PARA film. The samples were then shaken at 24° C. or 40° C. for 10 minutes. Subsequently, 50 ml of gas from each of the vials was passed through the gas-detecting tube for $CH_3SH$ (No. 71H, Gastech K.K.) to determine the concentration of the offensive odor remaining in the gas. The results are shown in Table 3.

The above phosphate buffer was prepared in the following manner: 500 ml each of 3.9 g of sodium dihydrogen phosphate·$2H_2O$ and 3.55 g of sodium hydrogen phosphate anhydride, both of which had been dissolved in distilled water, were mixed and adjusted to pH 7 or 6.5.

TABLE 3

| | Plant Extract | Reaction Temperature (° C.) | Degree of Deodorization by Enzyme Extract (%) | | | |
|---|---|---|---|---|---|---|
| | | | No Enzyme | Burdock | Pear | PPO |
| Example 10 | Rosemary (36.4 mg) | 24 | 0 | 100 | 100 | 100 |
| | | 40 | 0 | 100 | 100 | 100 |
| Example 11 | Raw coffee beans (7.2 mg) | 24 | 6 | 100 | 100 | 50 |
| | | 40 | 6 | 100 | 100 | 100 |
| Example 12 | Sunflower seeds (38.5 mg) | 24 | 0 | 100 | 100 | 56 |
| | | 40 | 0 | 100 | 100 | 100 |
| Example 13 | Tea (2.9 mg) | 24 | 0 | 12 | 56 | 56 |
| | | 40 | 0 | 58 | 96 | 85 |
| Example 14 | Grape seeds (7.7 mg) | 24 | 6 | 12 | 44 | 19 |
| | | 40 | 6 | 32 | 80 | 37 |
| Example 15 | Grape pericarp (10.1 mg) | 24 | 6 | 6 | 63 | 19 |
| | | 40 | 6 | 26 | 98 | 26 |
| Example 16 | Apple (2.7 mg) | 24 | 0 | 19 | 100 | 31 |
| | | 40 | 0 | 42 | 100 | 80 |

Examples 17 to 23

A predetermined amount (i.e. containing 2 mg of a phenolic compound) of each of the natural extracts as shown in Table 4 and 1.5ml of distilled water were introduced into a 100 ml vial. Also, ammonia or trimethylamine was added thereto at a final concentration of 100 ppm, and each vial was sealed with a PARA film. The samples were then shaken at room temperature for 10 minutes, and 50 ml of gas from each of the vials was measured for its ammonia or trimethylamine content by the appropriate gas-detecting tube for each offensive odor (No. 31 and No. 180, respectively, Gastech K.K.). The results are shown in Table 4. The same results were obtained regardless of whether any one of the plant enzymes (from burdock and pear) and PPO was used.

TABLE 4

| | Plant Extract | Degree of Deodorization of Offensive Odor (%) | |
|---|---|---|---|
| | | Ammonia | Trimethylamine |
| Example 17 | Rosemary | 100 | 100 |
| Example 18 | Raw coffee beans | 100 | 100 |
| Example 19 | Sunflower seeds | 100 | 100 |
| Example 20 | Tea | 100 | 100 |
| Example 21 | Grape seeds | 100 | 100 |
| Example 22 | Grape pericarp | 100 | 100 |
| Example 23 | Apple | 100 | 100 |

Examples 24 to 27

The following offensive odors were used as offensive odors encountered in daily living.

Solution of offensive odors;
(1) Garlic solution—One garlic bulb was smashed, then extracted with 1 liter of distilled water and filtered. The filtrate was used as a solution of a garlic offensive odor.
(2) Solution of tobacco odor—An aqueous solution of malodors from tobacco (prepared by allowing major smoke from 10 boxes of tobacco "Caster Mild" to be absorbed directly into 400 ml triethyl citrate) was diluted 50-fold and used as a solution of an offensive odor from tobacco.
(3) Malodors similar to matured persimmons (model odors of halitosis after drinking alcohol) were used to prepare a solution of offensive odors according to Japanese Patent Appln. Laid-Open Publication No. 16048/96 as follows.

| acetaldehyde | 362 ppm | isobutyl alcohol | 327 ppm |
|---|---|---|---|
| acetone | 93 ppm | isoamyl alcohol | 263 ppm |
| ethyl acetate | 263 ppm | ethanolamine | 82 ppm |
| ethyl alcohol | 45400 ppm | isobutyl amine | 60 ppm |
| n-propyl alcohol | 205 ppm | | |

The above aqueous solution.
(4) Solution of offensive odors—10-fold diluted aqueous solution of rat feces and urine The measurement of deodorization of offensive odors was carried out in the following manner.

Measurement Method 7.2 mg raw coffee bean extract (containing 2 mg polyphenol) and 17.2 mg burdock crude enzyme extract, 36.4 mg of rosemary extract and 50 mg pear crude enzyme extract, 38.5 mg sunflower seed extract and 50 mg pear crude extract, or 2.9 mg tea extract and 50 mg pear crude extract were added to a 100 ml vial. 1.5 ml of each of the solutions of the offensive odors was added to each vial and shaken for 10 minutes by hand. Then, the odors of the gas in each vial was actually smelled by 12 specialists. For comparison, 3 kinds of samples, namely, those not containing the crude enzyme extract, those not containing the natural extract and those not containing either of the enzyme extract and natural extract were prepared and treated in the same manner, and the odors in the gas were smelled and compared for evaluation. The results are shown in Table 5. As indicated in Table 5, "good" means good deodorizing activity.

TABLE 5

| Example | Offensive Odor | Pear & Rosemary | Pear & Sunflower Seeds | Pear & Tea | Burdock & Raw Coffee Beans |
|---|---|---|---|---|---|
| 24 | Garlic Odor | Good | Very Good | Slightly Good | — |
| 25 | Tobacco Odor | Very Good | Very Good | Slightly Good | — |
| 26 | Odors similar to Matured Persimmons | Very Good | Very Good | Slightly Good | — |
| 27 | Odor of Rat Feces and Urine | — | — | — | Good |

Example 28

3 g of chewing gum (A) containing a raw coffee bean extract (having a polyphenol content of 2 mg) and 10 mg burdock acetone powder was prepared. Separately, 3 g of chewing gum (B) containing a raw coffee bean extract (having a polyphenol content of 2 mg) was also prepared.

0.5 g of smashed garlic was placed in the mouth of Examinee (A) so that its odors were felt in the mouth, and the mouth was then washed with water. Chewing gum (A) was chewed for 10 minutes and breath from the mouth was collected in a polyester bag (TEDLAR®BAGS, 170×205 mm) and the odors in the bag were organoleptically evaluated by 12 panelists. The same procedure was carried out except that chewing gum (B) was chewed by Examinee (B). The results indicated that the breath from Examinee (A) was almost free of the odor, whereas the garlic odor remained in the breath from Examinee (B).

While the invention has been described in detail and with reference to specific embodiments thereof, it will be apparent to one skilled in the art that various changes and modifications can be made therein without departing from the spirit and scope thereof.

What is claimed is:

1. A deodorant composition for deodorizing methyl mercaptan comprising:
   (i) at least one natural extract containing a polyphenol, wherein said natural extract is selected from the group consisting of rosemary extract, sunflower seed extract, raw coffee bean extract, tea extract and apple extract; and
   (ii) an enzyme capable of oxidizing phenolic compounds.

2. The deodorant composition according to claim 1, wherein said natural extract contains from 2 to 100 mg of a polyphenol compound per 100 mg of the deodorant composition.

3. The deodorant composition according to claim 1, wherein said enzyme capable of oxidizing phenolic compounds is selected from the group consisting of polyphenol oxidase, monophenol oxidase, oxidase forming hydrogen peroxide and peroxidase.

4. The deodorant composition according to claim 1, comprising two or more natural extracts selected from the group consisting of rosemary extract, sunflower seed extract, raw coffee bean extract, tea extract and apple extract.

5. The deodorant composition according to claim 1, wherein said enzyme capable of oxidizing phenolic compounds comprises enzymes capable of oxidizing a phenolic compound into a compound having a quinone structure and enzymes capable of adding a phenolic hydroxy group for oxidation into quinone.

6. The deodorant composition according to claim 1, wherein said enzyme capable of oxidizing phenolic compounds is selected from the group consisting of laccase, tyrosinase, glucose oxidase and peroxidase.

7. The deodorant composition according to claim 1, comprising components (i) and (ii) in admixture.

8. A chewing gum comprising the deodorant composition of claim 1.

9. A deodorant composition for deodorizing methyl mercaptan comprising:
   (i) at least one natural extract containing a polyphenol, wherein said natural extract is selected from the group consisting of rosemary extract, sunflower seed extract, raw coffee bean extract, tea extract and apple extract; and
   (ii) a natural source containing an enzyme capable of oxidizing phenolic compounds.

10. The deodorant composition according to claim 9, wherein said natural source is selected from the group consisting of burdock, apple, pear and fungi.

11. A deodorant composition for deodorizing methyl mercaptan comprising:
    (i) at least one natural extract selected from the group consisting of rosemary extract, sunflower seed extract, raw coffee bean extract, tea extract and apple extract; and
    (ii) an enzyme capable of oxidizing phenolic compounds.

12. A deodorant composition as claimed in claim 1, wherein said natural extract is rosemary extract.

13. A deodorant composition as claimed in claim 1, wherein said natural extract is sunflower seed extract.

14. A deodorant composition as claimed in claim 1, wherein said natural extract is raw coffee bean extract.

15. A deodorant composition as claimed in claim 1, wherein said natural extract is tea extract.

16. A deodorant composition as claimed in claim 1, wherein said natural extract is apple extract.

* * * * *